(12) United States Patent
Wachsmuth (10) Patent No.: US 7,154,602 B2
(45) Date of Patent: Dec. 26, 2006

(54) METHOD FOR MEASURING FLUORESCENCE CORRELATIONS IN THE PRESENCE OF SLOW SIGNAL FLUCTUATIONS

(75) Inventor: Malte Wachsmuth, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 406 days.

(21) Appl. No.: 10/868,997

(22) Filed: Jun. 16, 2004

(65) Prior Publication Data

US 2004/0257562 A1 Dec. 23, 2004

(30) Foreign Application Priority Data

Jun. 17, 2003 (DE) ................. 103 27 531

(51) Int. Cl.
*G01N 21/25* (2006.01)
(52) U.S. Cl. .......................... 356/417; 356/317
(58) Field of Classification Search .............. 356/417, 356/317; 250/559.06
See application file for complete search history.

(56) References Cited

U.S. PATENT DOCUMENTS 5,764,363 A * 6/1998 Ooki et al. ................. 356/364
6,720,547 B1 * 4/2004 Rajadhyaksha et al. ..... 250/225
6,867,919 B1 * 3/2005 Seyfried ..................... 359/618
2002/0027709 A1 * 3/2002 Engelhardt et al. ......... 359/385
2004/0238730 A1 * 12/2004 Langowski et al. ......... 250/234
2004/0257646 A1 * 12/2004 Wachsmuth ................ 359/385

FOREIGN PATENT DOCUMENTS

| DE | 197 57 740 C2 | 7/1999 |
|----|---------------|--------|
| DE | 199 49 658 A1 | 5/2001 |
| DE | 100 08 594 A1 | 8/2001 |
| DE | 101 15 309 A1 | 10/2002 |
| JP | 2001194305 | 7/2001 |

* cited by examiner

Primary Examiner—Gregory J. Toatley, Jr.
Assistant Examiner—Roy M. Punnoose
(74) Attorney, Agent, or Firm—Houston Eliseeva LLP (57) ABSTRACT

A method for measuring fluorescence correlations in the presence of slow signal fluctuations using a scanning microscope is disclosed. An illuminating light beam is positioned, with the scanning module, for a specific time period on a location of the specimen. Either a direct filtering is performed on the acquired data, or a Fourier analysis is performed. A suitable filter is then used to perform a filtering of the data subjected to the Fourier analysis. Lastly, a correlation function is calculated exclusively on the filtered data.

21 Claims, 9 Drawing Sheets

METHOD FOR MEASURING FLUORESCENCE CORRELATIONS IN THE PRESENCE OF SLOW SIGNAL FLUCTUATIONS

RELATED APPLICATIONS

This application claims priority of the German patent application 103 27 531.2 which is incorporated by reference herein.

FIELD OF THE INVENTION

The invention concerns a method for measuring fluorescence correlations in the presence of slow signal fluctuations. The invention concerns in particular a method for determining diffusion and transport processes using a scanning microscope that encompasses a deflection means for coupling in an illuminating light beam and a scanning module for graphical depiction of a specimen on a peripheral device and for positioning the illuminating light beam for a specific time period on a location of the specimen.

BACKGROUND OF THE INVENTION

Fluorescence correlation spectroscopy (FCS) and related methods, in their implementation in a microscope assemblage, are suitable for the investigation of molecular mobility and interactions in microscopic measurement volumes smaller than one femtoliter (1 fl $=10^{-15}$ liter) and at low concentrations of less than 1 μMol (μM). In typical FCS experiments with a stationary measurement volume and, in particular, in aqueous solution, the average number of fluorescent-labeled molecules present in the measurement volume is low (<1,000). Brownian motion of the molecules causes their number to fluctuate about that average, resulting in corresponding fluctuations in the fluorescence signal about an average. Autocorrelation analysis of one detection channel and/or cross-correlation analysis of more than one detection channel makes possible a quantitative determination of, for example, the concentrations and diffusion properties of several fluorescent-labeled species and their interactions with one another.

In structured samples in particular, for example in biological cells, additional and often dominant fluctuations (especially drift) can occur in the signal. The slow motions of cell structures are one example. These motions are overlaid on the diffusion-related molecular motions.

A further influence on the measurement result is exerted by fluorescent-labeled molecules that are transiently or permanently immobilized by binding onto cell structures. Under illumination, their fluorescence typically is irreversibly extinguished after times ranging from 100 msec to seconds. This is referred to as "photobleaching."

Very slow fluorescent aggregates, moving slowly through the measurement volume as a singular event, may likewise be present. Combinations of the above-described influences on measurement results are conceivable.

When the correlation functions of the signals are calculated, these drifts and fluctuations often constitute dominant contributions that overlie the molecular-diffusion contributions of interest, and often make them impossible to evaluate. While analytical or numerical models permitting a quantitative evaluation do exist for the correlation function of signal fluctuations as a result of molecular diffusion, such is not (or very seldom) the case for the instances mentioned.

In conventional FCS, therefore, slow fluctuations make evaluation difficult or impossible.

The existing art corresponds to the implementation of FCS experiments using the commercially available FCS units/correlators of ALV (ALV-Laser-Vertriebsgesellschaft mbH, Langen, Germany), ISS (ISS Inc., Champaign, Ill., USA), and Zeiss (Carl Zeiss Jena GmbH, Jena, Germany).

SUMMARY OF THE INVENTION

It is the object of the invention to create a method with which the molecular diffusion in a specimen or a sample can be determined, while preventing distortion of the molecular diffusion measurement result due to interfering influences that also exist in the specimen.

The object is achieved by way of a method comprising the steps of:

providing a deflection means for coupling in an illuminating light beam, providing a scanning module for graphical depiction of a specimen on a peripheral device, and at least one detector for photon counting, acquiring the data, the illuminating light beam being positioned, with the scanning module, for a specific time period on a location of the specimen;

directly filtering the acquired data; and calculating a correlation function.

The method for measuring fluorescence correlations in the presence of slow signal fluctuations using a scanning microscope is advantageous because a deflection means for coupling in an illuminating light beam, a scanning module for graphical display of a specimen on a peripheral device, and at least one detector for photon counting, for example an avalanche photodiode, is provided. Firstly, data acquisition is accomplished, the illuminating light beam being positioned, with the scanning module, for a specific time period on a location of the specimen. Either the acquired data are subjected directly to filtering, or a Fourier analysis is performed on the acquired data. Filtering of the data subjected to the Fourier analysis is then accomplished using a suitable filter. Lastly, calculation of a correlation function is performed exclusively on the filtered data. Filtering of the data is implemented in software or in a combination of hardware and software.

A selectable filter can encompass a short-pass filter that filters slow fluctuations (processes >100 ms) out of the acquired data. A further possibility for a filter is a long-pass filter that filters out fast fluctuations (processes typically in the μs to ms range); this corresponds to a lengthening of the sampling time upon recording of the fluorescence signal. The calculated correlation function then describes only slow fluctuations whose time range is well above one msec, thus allowing the method to be linked to time-lapse imaging, so that the measured values for the correlation analysis can be used directly from the images acquired with the scanning microscope. The slow fluctuations are used to analyze the dynamics of cell structures.

A further advantageous filtering method is the fact that a bandpass filter is provided which defines an upper and a lower limit, so that fluctuations below the lower limit and above the upper limit are filtered out. In addition, using a band-blocking filter or notch filter, it is possible to filter out fluctuations between an upper and a lower limit or around a central frequency, so that upon calculation of the correlation function, only the fluctuations of interest below the lower limit and above the upper limit are described. Temporary significant deviations of the acquired data beyond a statistically expected amount are automatically detected by setting an upper and a lower threshold, so that those regions are then excised from the acquired data and not used for the correlation analysis. The temporary significant deviations as a result of fluorescing molecular aggregates, or those caused by the attachment of fluorescing molecules to less mobile components of the specimen (15), are thereby eliminated.

An empirical trend curve is used to detect slow fluctuations—especially drift due to photobleaching—and to perform an evaluation, the empirical trend curve being a polynomial or a sum of exponential curves. A scaled difference between the acquired data and the trend curve is calculated, and then contains only the diffusion-related fluctuations of interest that are captured by correlation analysis.

Further advantageous embodiments of the invention may be inferred from the dependent claims.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
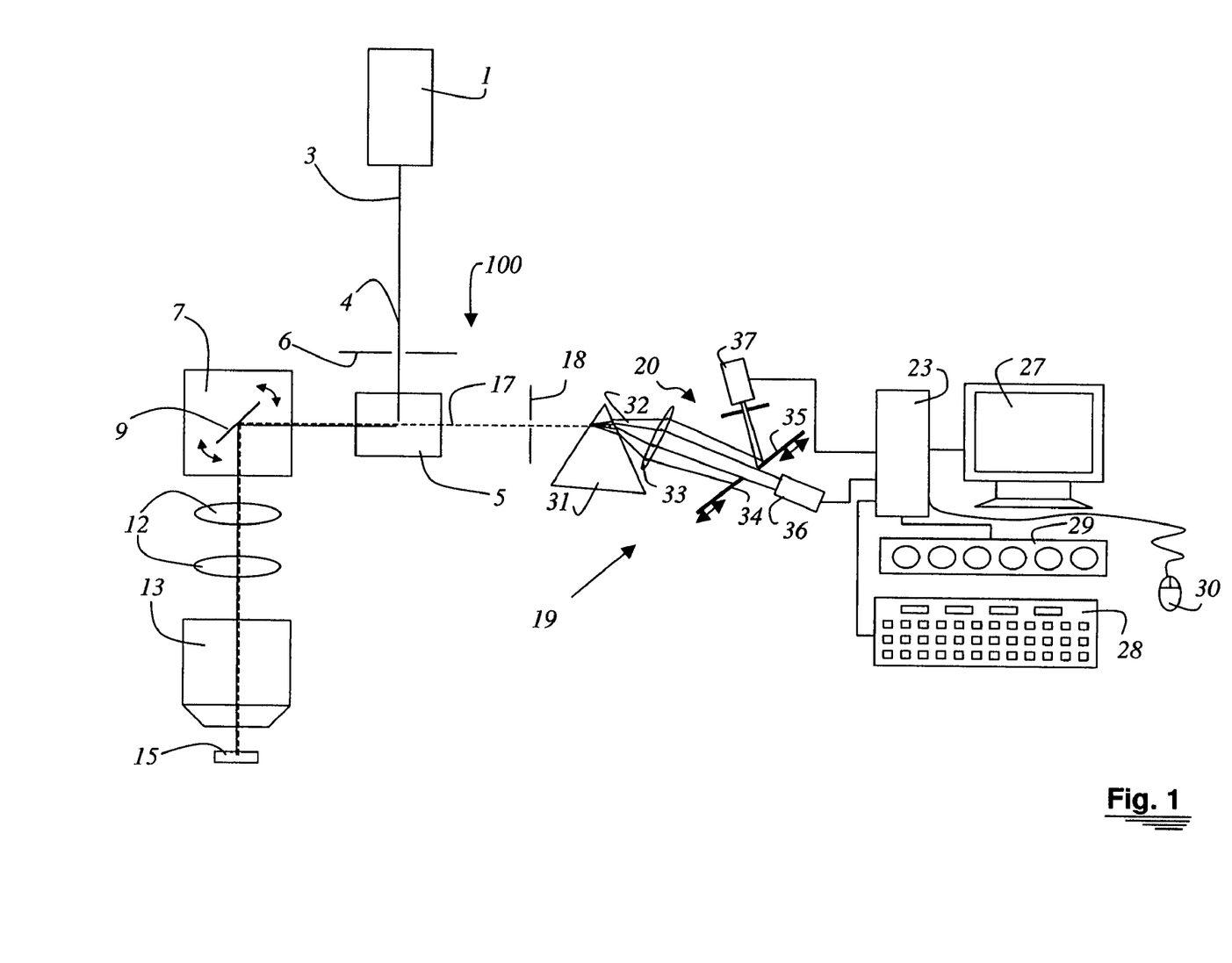
FIG. 1 schematically depicts a scanning microscope having an SP module.

FIG. 1 shows the schematic configuration of a confocal scanning microscope 100 that is used in the method according to the present invention. Illuminating light beam 3 coming from at least one illumination system 1 is directed by a beam splitter or a suitable deflection means 5 to a scanning module 7. Before illuminating light beam 3 strikes deflection means 5, it passes through an illumination pinhole 6. Scanning module 7 encompasses a gimbal-mounted scanning mirror 9 that guides illuminating light beam 3, through a scanning optical system 12 and a microscope optical system 13, over or through a specimen 15. In the case of non-transparent specimens 15, illuminating light beam 3 is guided over the specimen surface. With biological specimens 15 (preparations) or transparent specimens, illuminating light beam 3 can also be guided through specimen 15. For these purposes, non-luminous preparations are prepared, if applicable, with a suitable dye (fluorescent marker) (not depicted, since it is established existing art). The dyes present in the specimen are excited by illuminating light beam 3 and emit light in a characteristic region of the spectrum peculiar to them. This light proceeding from specimen 15 defines a detected light beam 17. The latter travels through microscope optical system 13 and scanning optical system 12 and via scanning module 7 to deflection means 5, passes through the latter, and arrives via a detection pinhole 18 at at least one detector 19, which is embodied as a photomultiplier. It is clear to one skilled in the art that other detection components, for example diodes, diode arrays, photomultiplier arrays, CCD chips, or CMOS image sensors, can also be used. Detected light beam 17 proceeding from and defined by specimen 15 is depicted in FIG. 1 as a dashed line. Electrical detected signals proportional to the power level of the light proceeding from specimen 15 are generated in detector 19. Because, as already mentioned above, light of more than one wavelength is emitted from specimen 15, it is advisable to insert in front of the at least one detector 19 a selection means for the spectrum proceeding from the sample. In the embodiment shown here, the selection means is an SP module 20. SP module 20 is embodied in such a way that it can acquire a complete lambda scan, i.e. all the wavelengths proceeding from specimen 15 are recorded. The data generated by detector 19 are forwarded to a computer system 23. At least one peripheral device 27 is associated with computer system 23. Peripheral device 27 can be, for example, a display on which the user receives instructions for setting the scanning microscope or can view the current setup and also the image data in graphical form. Also associated with computer system 23 is an input means that comprises, for example, a keyboard 28, an adjusting apparatus 29 for the components of the microscope system, and a mouse 30. Detected light beam 17 is spatially spectrally divided with a prism 31. A further possibility for spectral division is the use of a reflection or transmission grating. The spectrally divided light fan 32 is focused with focusing optical system 33, and then strikes a mirror stop arrangement 34, 35. Mirror stop arrangement 34, 35, the means for spectral spatial division, focusing optical system 33, and detectors 36 and 37 are together referred to as the SP module (or multi-band detector) 20.

Figure 2:
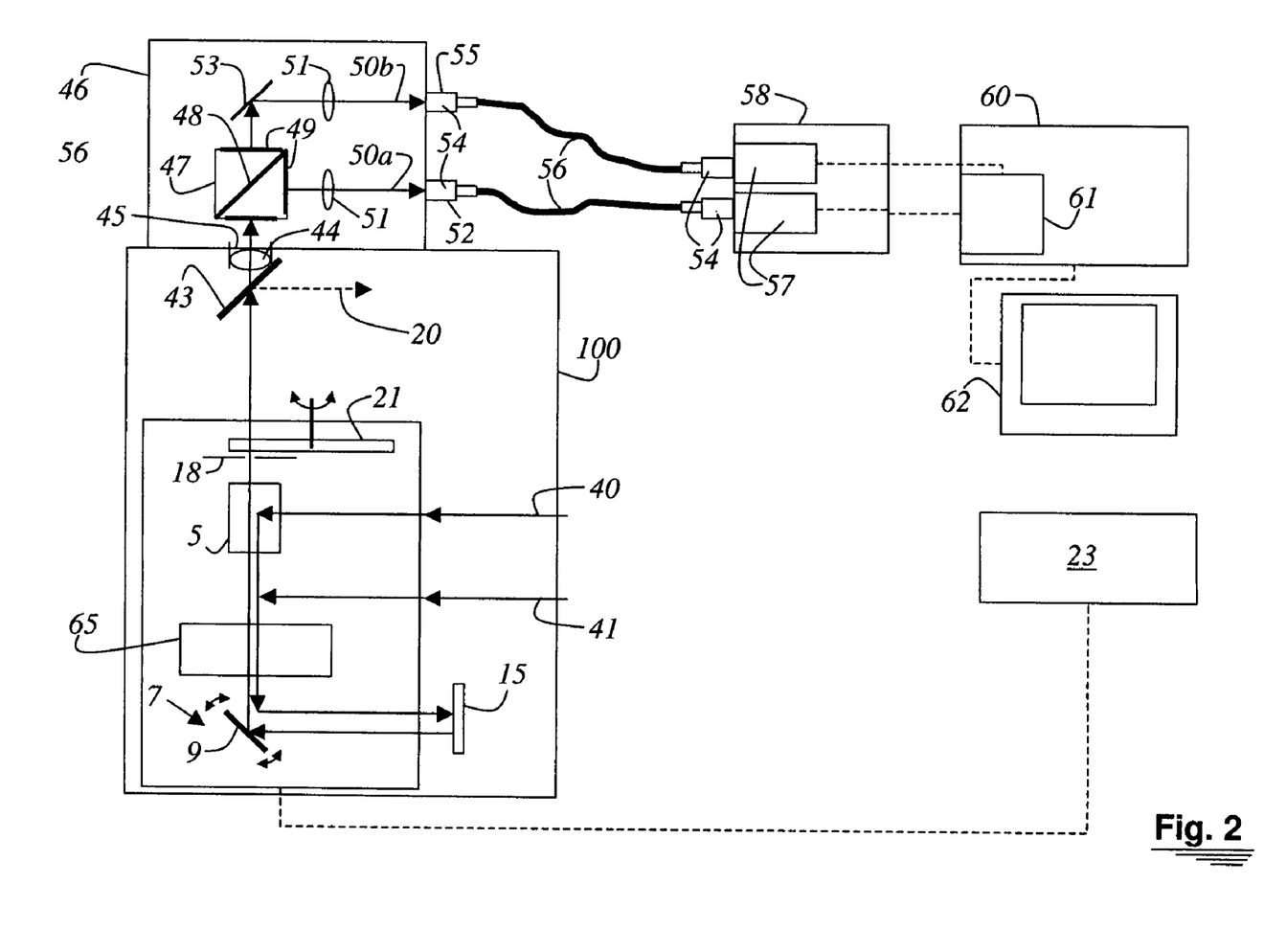
FIG. 2 schematically depicts the arrangement of the device components for FCS analysis in a scanning microscope.

FIG. 2 schematically depicts the arrangement of several device components for FCS analysis in scanning microscope 100. A conventional scanning microscope 100, with which a conventional SP module 20 is associated, is used for the FCS analysis. Scanning microscope 100 is equipped with a deflection means 5 that functions as the main beam splitter and is embodied as a beam splitter slider or AOBS™. As already described in FIG. 1, all available visible laser lines can be coupled in via a first input 40 as light sources. Incoupling of UV radiation or IR radiation, which is usable for multi-photon applications (and also FCS), is accomplished via a second input 41. In FIG. 2, the beam direction toward SP module 20 is indicated by a dashed arrow. The detected light (light proceeding from specimen 15) passes through microscope optical system (not depicted in FIG. 2), scanning mirror 9, deflection means 5, detection pinhole 18, optionally a filter wheel 21 to block out the excitation light, and an adjustable beam splitter slider 43, which contains a mirror for complete deflection into SP module 20, a beam splitter or a single substrate for partial deflection into SP module 20, or an empty space. The beam of detected light is collimated by a downstream lens 44. Located behind this lens 44 is an output 45 out of the stand of scanning microscope 100. Mounted above this output 45 is a housing 46 in which a changeable filter cube 47 is located. At (removable) beam splitter 48 that is provided in filter cube 47, the detected light is split into two components, e.g. into a "red" component 50a and a "blue" component 50b. Additional filters 49 provide further blocking of the excitation light and of other undesired light components. These are optional when an AOBS is used as deflection means 5. One sub-beam, for example "red" component 50a, is then focused with a lens 51 directly onto first detection channel 52. The second sub-beam, for example "blue" component 50b, is focused via an additional deflection mirror 53, likewise with a lens 51, onto a second detection channel 55. Each channel is made up of a standard FC socket 54, a standard multimode fiber 56 having a light-tight sheath and equipped with an FC connector at each of the two ends, a further FC socket 54, and an avalanche photodiode (APD) 57. APDs 57 are characterized by their particularly high detection efficiency as compared with photomultiplier tubes, especially in the visible wavelength region. The two APDs 57 are accommodated together in one housing 58, to ensure sufficient cooling and light-tightness of the detectors. The signals of APDs 57 are then conveyed into a computer 60 that is responsible for the FCS analysis. A detector board 61 is provided in computer 60. Connected to computer 62 is an additional monitor 62 on which the measurement results can be displayed in a wide variety of ways. As already described in FIG. 1, scanning microscope 100 has an "independent" computer 23 that is likewise equipped with an independent peripheral device 27. The peripheral device encompasses, for example, two monitors that belong to scanning microscope 100 as standard equipment. All the control of scanning module 7 and scanning mirrors 9 provided therein, and detection using SP module 20, is executed via computer system 23.

The method proceeds, in general, in such a way that firstly a confocal overview image of specimen 15 is acquired. One or more points of interest in the image are then identified, e.g. by marking with the cursor, and the illuminating light beam or beams is/are parked there for a specific time. Beam splitter slider 43 directly in front of output 45 is then set to the empty space or the single substrate. The single substrate has the advantage that one can switch over more quickly between confocal image acquisition and FCS, since no mirror sliders need to be moved between images. FCS imaging and SP module 20 can then be used more or less simultaneously. The fluorescent light is then focused onto the two detection channels 52 and 55. The APDs provide photon counting. The signal is then conveyed to detector board 61. An evaluation of the signal (including calculation of the autocorrelation and cross-correlation) is then performed using a software program, and the result is displayed on additional monitor 62. This method is typically used to determine diffusion rates, concentrations, chemical bonds, etc.

Figure 3:
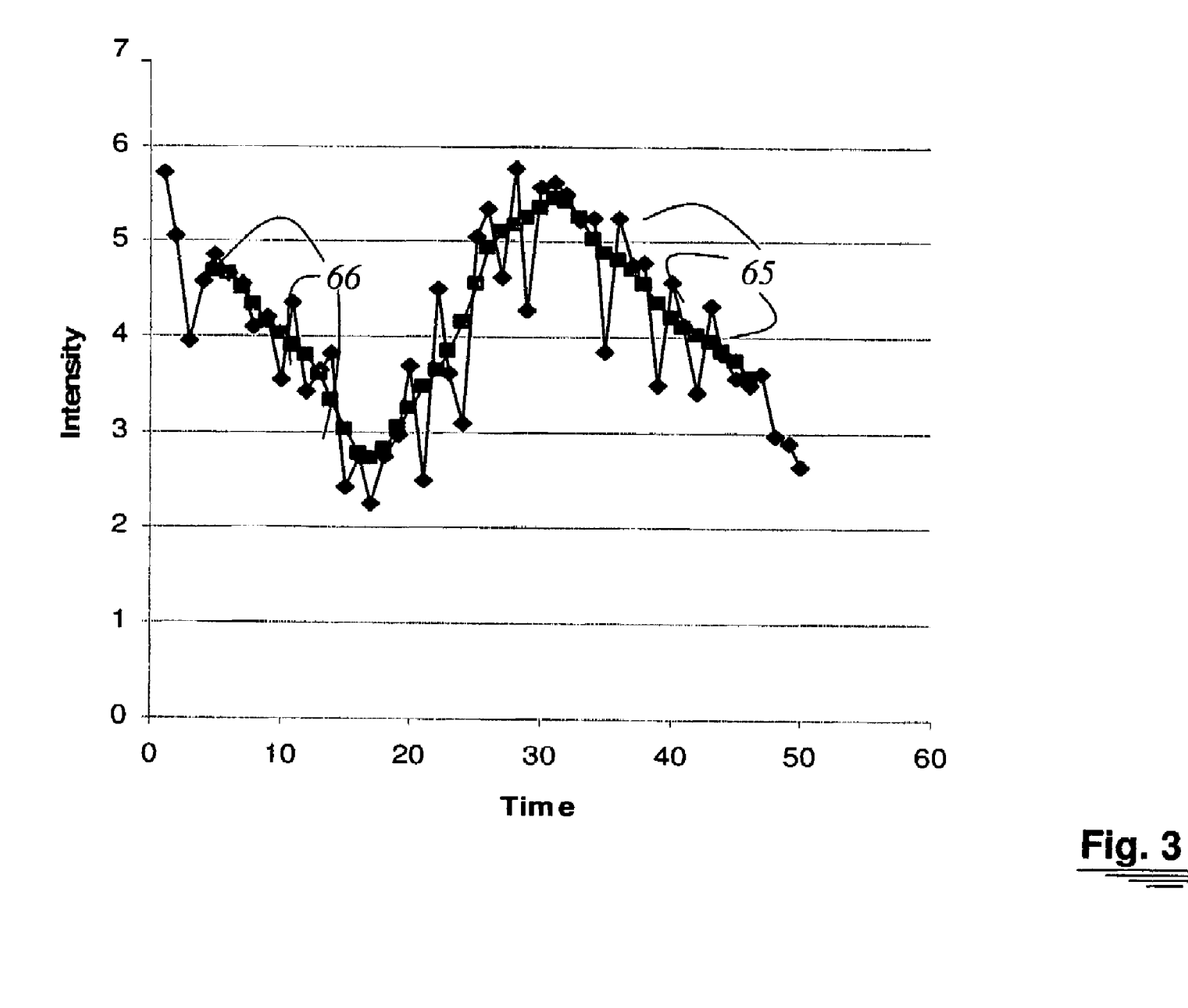
FIG. 3 graphically depicts the measured FCS raw data compared with data that have been filtered using a low-pass filter.

FIG. 3 graphically depicts data 65 measured by means of avalanche photodiode (APD) 57, which are FCS raw data, compared with data 66 that have been filtered with a low-pass filter. Time in microseconds (μs) is plotted on the abscissa. The time describes the time period within which data are acquired with avalanche photodiode 57. The intensity, or the number of photons recorded per unit time, is plotted on the ordinate. Measured data 65 are represented by diamonds. Data 66 filtered with the low-pass filter are depicted with squares. The filtering yields a curve with reduced peaks. The fluorescence correlations are determined in the presence of slow signal fluctuations using a scanning microscope 100, the scanning microscope encompassing a deflection means 5 for coupling in an illuminating light beam 3, a scanning module 7 for graphical display of a specimen 15 on a peripheral device 27, and at least one avalanche photodiode 57 for photon counting. The data are acquired in the context of determination of the fluorescence correlations, scanning module 7 being used to position the illuminating light beam for a specific time period at a location of specimen 15. After direct filtering, or filtering of the data subjected to a Fourier analysis, calculation of a correlation function is performed. As depicted in FIG. 3, in one embodiment the filtering is performed with a short-pass filter in order to filter slow fluctuations out of the acquired data.

Figure 4:
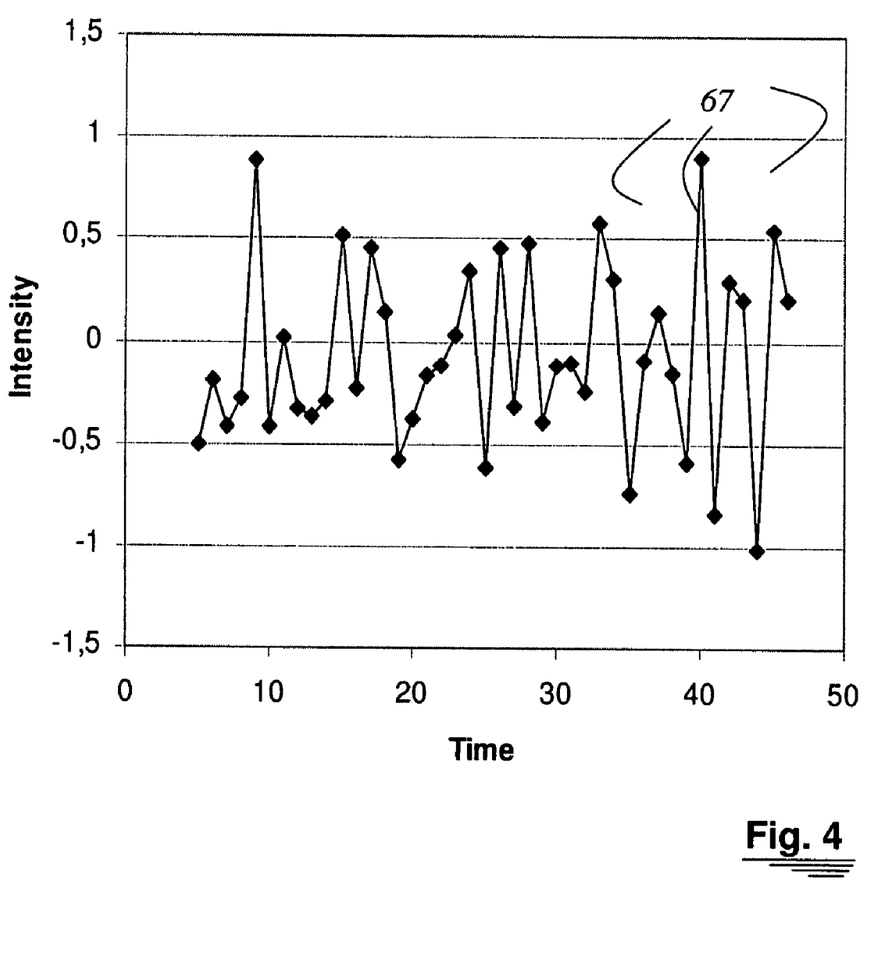
FIG. 4 graphically depicts the measured FCS raw data compared with data that have been filtered using a high-pass filter.

FIG. 4 graphically depicts filtered data, the measured FCS raw data having been filtered with a high-pass filter. Time in microseconds (μs) is plotted on the abscissa. The time describes the time period within which data are acquired with avalanche photodiode 57. The intensity, or the number of photons recorded per unit time, is plotted on the ordinate in relative units. Data 67 filtered with the high-pass filter are depicted in FIG. 4 using diamonds. The filtering encompasses a long-pass filter that filters out fast fluctuations, corresponding to a lengthening of the sampling time upon recording of the fluorescence signal. The calculated correlation function then describes only slow fluctuations whose time range is well above one msec, thus allowing the method to be linked to time-lapse imaging, so that the measured values for the correlation analysis can be used directly from the images acquired with the scanning microscope. The slow fluctuations are used to analyze the dynamics of cell structures.

Figure 5:
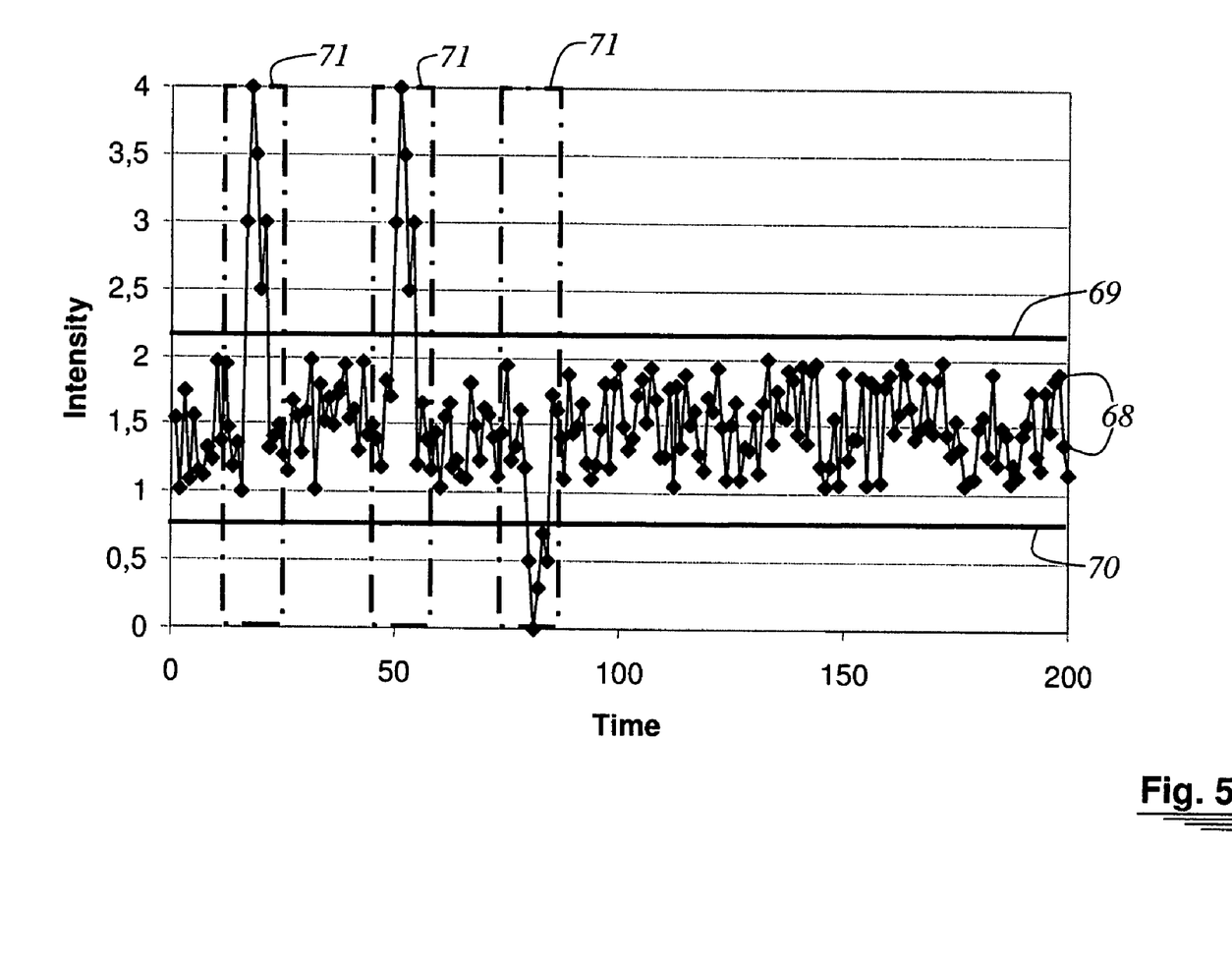
FIG. 5 graphically depicts the measured FCS raw data filtered by setting an upper and a lower threshold and by masking prior to correlation calculation.

FIG. 5 is a graphical depiction of the measured FCS raw data (acquired data 68 being depicted in FIG. 5 using diamonds) that are filtered by setting an upper and a lower threshold 69 and 70 and by means of at least one mask 71 prior to correlation calculation. Time in seconds is plotted on the abscissa. The time describes the time period within which data are acquired with avalanche photodiode 57. The intensity, or the number of photons recorded per unit time, is plotted on the ordinate. Mask 71 is implemented in those regions of acquired data 68 at which irregularities occur as compared with the rest of the acquired data 68. The temporary significant deviation of acquired data 68 beyond a statistically expected amount can be automatically detected by setting upper and lower thresholds 69 and 70, so that the regions identified by mask 71 can then be excised from acquired data 68 and not used for the correlation analysis. Computer 60 automatically identifies upper and lower thresholds 69 and 70 and mask 71, so that the latter can be automatically plotted on the display and indicated to the user.

Figure 6:
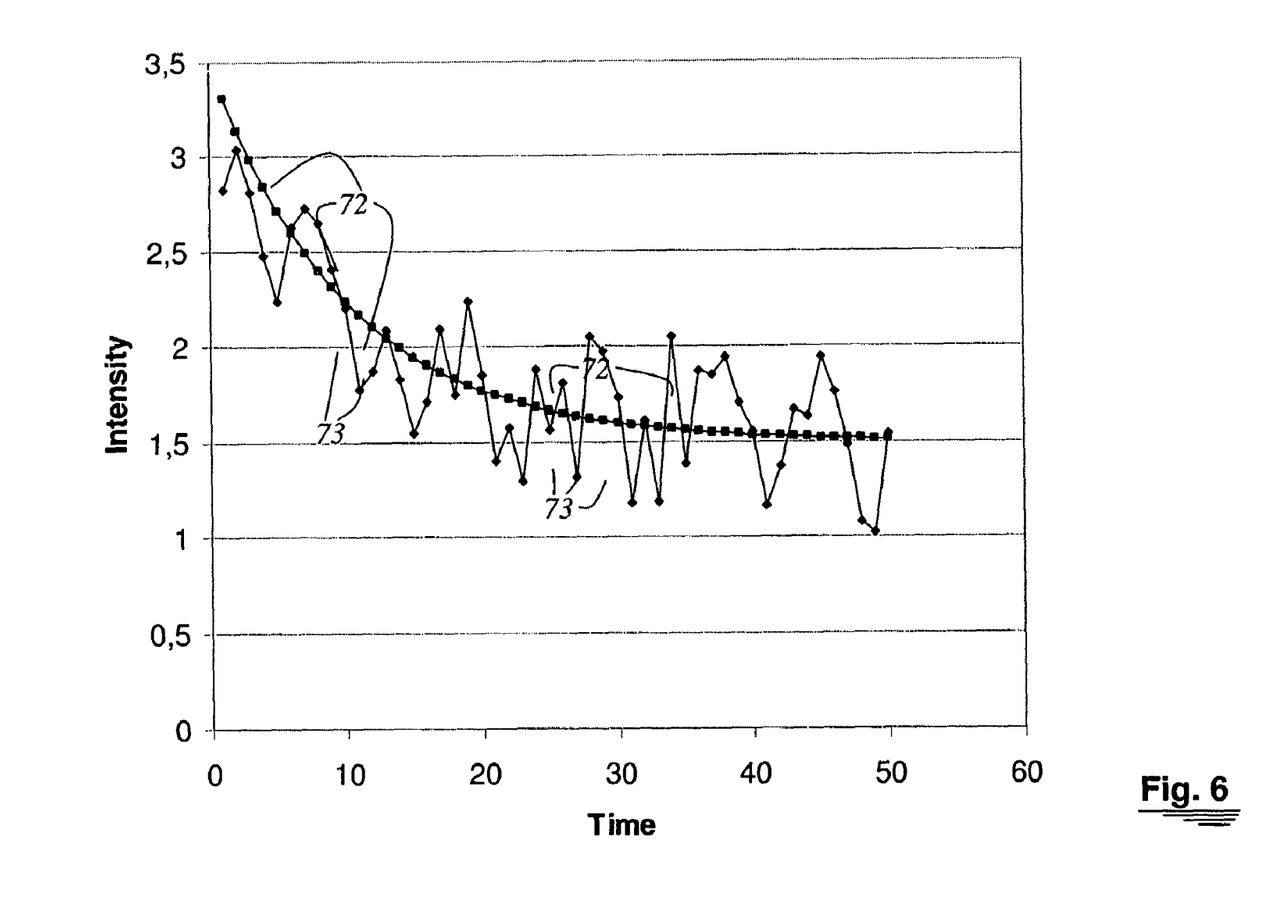
FIG. 6 graphically depicts the raw data resulting from photobleaching, compared with the data that have been adapted with a model.
Figure 7:
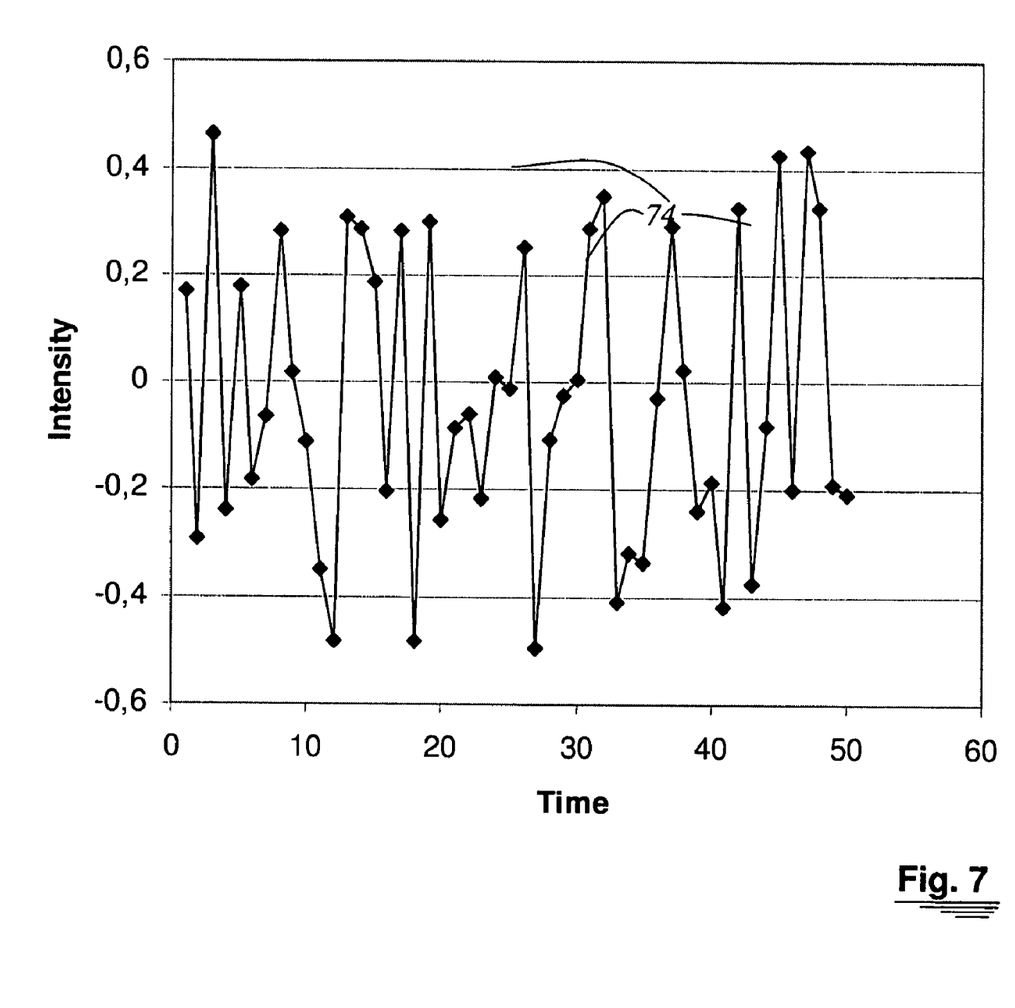
FIG. 7 graphically depicts a corrected signal from FIG. 6.

FIG. 6 graphically depicts the raw data resulting from photobleaching, compared with the data that have been adapted using a model. Measured data 72 are depicted as diamonds, and data 73 adapted with the model as squares. Measured data 72 are adapted by means of an empirical trend curve that can be a polynomial or a sum of exponential curves. FIG. 7 graphically depicts a corrected signal 74 from FIG. 6. The suitably scaled difference between the measured data and the trend curve then contains only the diffusion-related fluctuations of interest that can be captured by correlation analysis.

Figure 8:
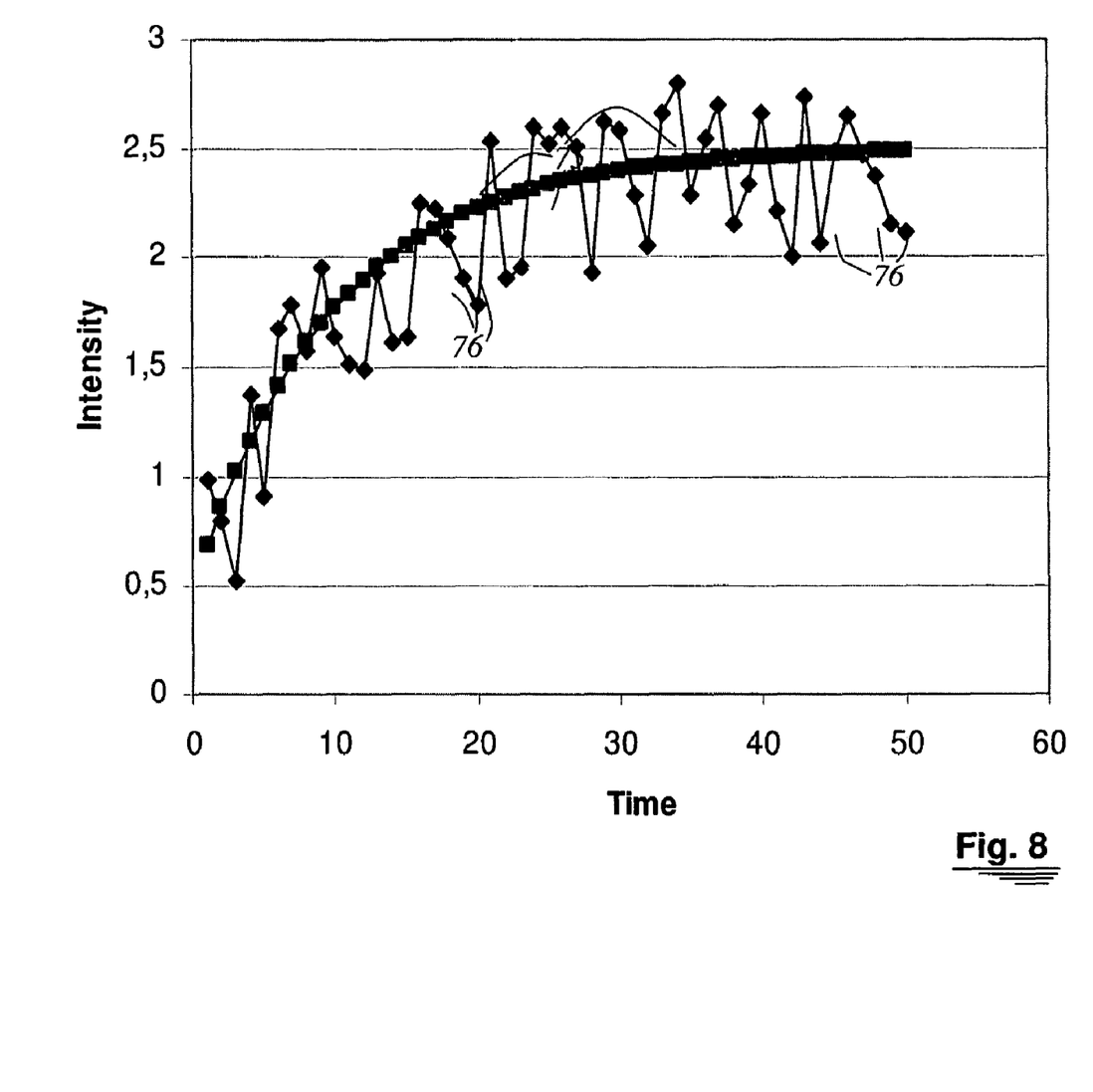
FIG. 8 graphically depicts the increase in the raw data occurring after rapid bleaching, compared with the data that have been adapted with a model.
Figure 9:
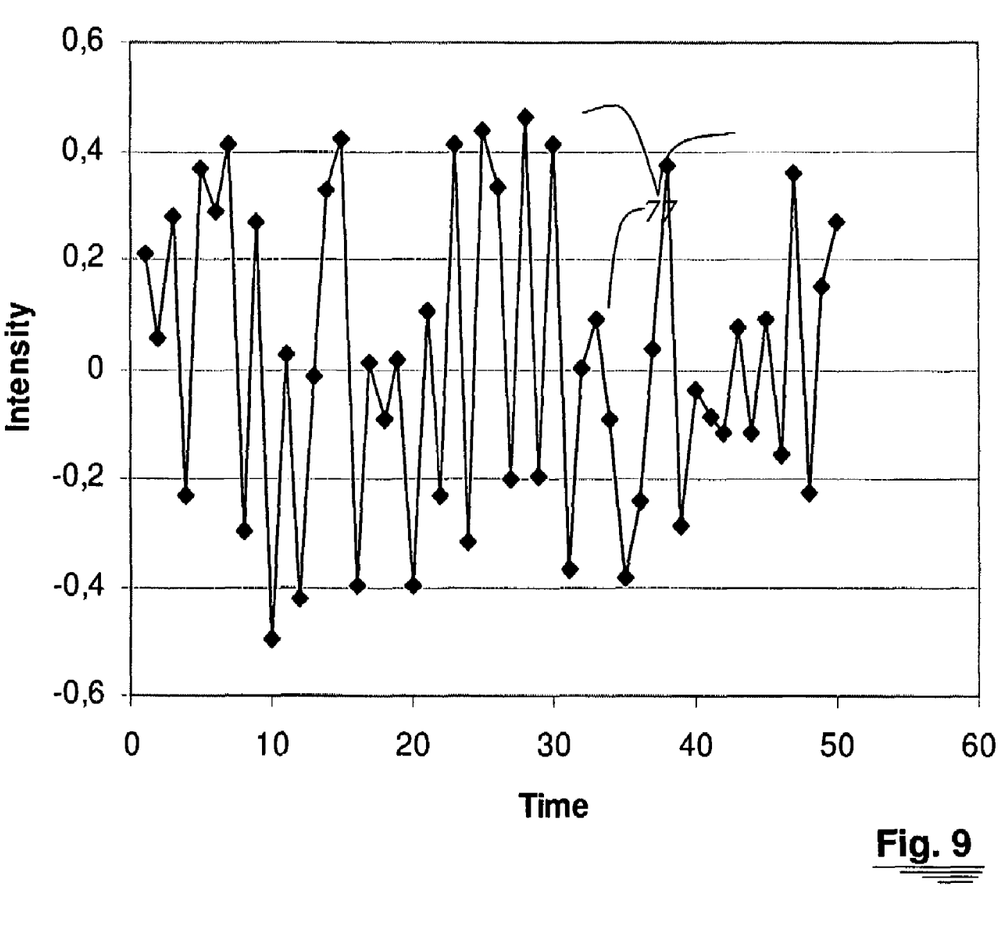
FIG. 9 graphically depicts a corrected signal from FIG. 8.

FIG. 8 graphically depicts the increase in the raw data, or measured data 75, occurring after rapid bleaching (photobleaching). Measured data 75 are also depicted in comparison with adapted data 76 that have been adapted with a model. A spot-FRAP experiment can be performed in an experimental setup suitable for FCS. The time profile of the increase occurring again after bleaching is determined by diffusion and by the permanent or transient immobilization of the fluorescent molecules, and can be adapted with the model. The suitably scaled difference between the adapted model function and the original signal then contains only the diffusion-related fluctuations of interest that can be captured by correlation analysis. A simultaneous quantitative description of the diffusion-related and binding-related contributions to molecular mobility is thus possible. FIG. 9 graphically depicts corrected signal 77 from FIG. 8.

What is claimed is:

1. A method for determining fluorescence correlations in the presence of slow signal fluctuations using a scanning microscope comprises the steps of:
   providing a deflection means for coupling in an illuminating light beam,
   providing a scanning module for graphical depiction of a specimen on a peripheral device, and at least one detector for photon counting,
   aquiring data generated by the detector, the illuminating light beam being positioned, with the scanning module, for a specific time period on a location of the specimen;
   directly filtering the acquired data; and
   calculating a correlation function, and providing an output that is representative of fluorescence correlations in the presence of slow signal fluctuations.

2. The method as defined in claim 1, wherein first a Fourier analysis is performed on the acquired data, and then a filtering of the data subject to the Fourier analysis.

3. The method as defined in claim 1, wherein the filtering step encompasses a short-pass filter that filters slow fluctuations out of the acquired data.

4. The method as defined in claim 1, wherein the filtering encompasses a long-pass filter that filters out fast fluctuations, corresponding to a lengthening of the sampling time upon recording of the fluorescence signal.

5. The method as defined in claim 4, wherein the calculated correlation function describes only slow fluctuations whose time range is well above one msec, thus allowing the method to be linked to time-lapse imaging, so that the measured values for the correlation analysis can be used directly from the images acquired with the scanning microscope.

6. The method as defined in claim 5, wherein the slow fluctuations are used to analyze the dynamics of cell structures.

7. The method as defined in claim 1, wherein the filtering encompasses a bandpass filter that defines an upper and a lower limit, so that fluctuations below the lower limit and above an upper limit are filtered out.

8. The method as defined in claim 7, wherein temporary significant deviations of the acquired data beyond a statistically expected amount are automatically detected by setting an upper and a lower threshold, so that those regions are then excised from the acquired data and not used for the correlation analysis.

9. The method as defined in claim 1, wherein the filtering is performed with a band-blocking filter or notch filter, fluctuations between an upper and a lower limit or around a central frequency are filtered out, so that upon calculation of the correlation function, only the fluctuations of interest below the lower limit and above the upper limit are described.

10. The method as defined in claim 9, wherein the temporary significant deviations are caused by fluorescing molecular aggregates, or by the attachment of fluorescing molecules to less mobile components of the specimen.

11. The method as defined in claim 1, wherein an empirical trend curve is used in order to adapt slow fluctuations, in particular drift due to photobleaching.

12. The method as defined in claim 11, wherein the empirical trend curve is a polynomial or a sum of exponential curves.

13. The method as defined in claim 11, wherein a scaled difference between the acquired data and the trend curve is calculated, and then contains only the diffusion-related fluctuations of interest that are captured by a correlation analysis.

14. The method as defined in claim 1, wherein a continuous decrease in the signal resulting from photobleaching, caused by permanently or transiently immobilized molecules, is adapted with the aid of suitable analytical model functions using the scanning microscope, a suitably scaled difference between the adapted model function and the acquired data then containing only the diffusion-related fluctuations of interest.

15. The method as defined in claim 14, wherein the diffusion-related and binding-related contributions to molecular mobility are simultaneously quantitatively described therefrom.

16. The method as defined in claim 1, wherein a spot-FRAP experiment is performed with the scanning microscope, the time profile of the increase occurring again in a signal after bleaching being determined by diffusion and by the permanent or transient immobilization of the fluorescent molecules, and being adapted with model functions.

17. The method as defined in claim 1, wherein the suitably scaled difference between the adapted model function and the acquired data then contains only the diffusion-related fluctuations of interest that are captured by correlation analysis, the diffusion-related and binding-related contributions to molecular mobility being simultaneously quantitatively described.

18. The method as defined in claim 1, wherein a detected light beam is directed onto a beam splitter provided in a housing, and from there travels to a first and second detection channel.

19. The method as defined in claim 18, wherein the detected light beam is conveyed by a respective multimode fiber from the first and second detection channel to the at least one avalanche photodiode.

20. The method as defined in claim 18, wherein an autocorrelation function is calculated from the detected signals generated by the data obtained through the first detection channel and the second detection channel.

21. The method as defined in claim 1, wherein the detected signals are obtained using at least one avalanche photodiode; and the acquired data are conveyed to a computer that performs the FCS analysis.

* * * * *